US00PP28112P3

(12) United States Plant Patent
O'Connell

(10) Patent No.: US PP28,112 P3
(45) Date of Patent: Jun. 13, 2017

(54) ***ECHEVERIA* PLANT NAMED 'GALAXIA'**

(50) Latin Name: ***Echeveria* hybrid**
Varietal Denomination: Galaxia

(71) Applicant: Renee O'Connell, Escondido, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 48 days.

(21) Appl. No.: 14/756,704

(22) Filed: Oct. 1, 2015

(65) Prior Publication Data

US 2017/0099760 P1 Apr. 6, 2017

(51) Int. Cl.
*A01H 5/00* (2006.01)

(52) U.S. Cl.
USPC ..... Plt./373

(58) Field of Classification Search
USPC ..... Plt./263.1, 373
See application file for complete search history.

*Primary Examiner* — Keith Robinson
(74) *Attorney, Agent, or Firm* — Cassandra Bright

(57) ABSTRACT

A new and distinct *Echeveria* cultivar named 'Galaxia' is disclosed, characterized by compact, concentric rosettes comprised of blue-violet leaves with rose margins. Plants freely offset, enabling increased and faster propagation of the cultivar. Robust growth, in combination with the freely offsetting, results in clusters at an early age, enhancing production intervals, as well as creating an aesthetically superior product for the consumer. The new variety is an *Echeveria*, part of the Crassulaceae complex that includes *Aeonium, Cotyledon, Graptopetalum, Pachyphytum, Sedum* and others. *Echeveria* is a popular genus, typically produced as container plants for the patio or as landscape plants.

4 Drawing Sheets

Latin name: *Echeveria* hybrid.
Varietal denomination: 'Galaxia'.

BACKGROUND OF THE INVENTION

The new cultivar, *Echeveria* 'Galaxia' is the product of a planned breeding program. The new variety originated from a cross pollination of the proprietary, unpatented, seed parent, *Echeveria* 'ENC07' with the pollen parent, an unpatented, proprietary pollen parent *Echeveria* 'AG2B'. The cross pollination was made during April 2011 in Vista, Calif., at a commercial greenhouse. 'Galaxia' was discovered by the inventor, Renee O'Connell, in September 2011, in Vista, Calif. at a commercial greenhouse in Vista, Calif.

Asexual reproduction of the new cultivar 'Galaxia' was first performed in Vista, Calif., at a commercial greenhouse, by vegetative cuttings in December, 2011. *Echeveria* 'Galaxia' has since produced multiple generations and has shown that the unique features of this cultivar are stable and reproduced true to type.

SUMMARY OF THE INVENTION

The cultivar 'Galaxia' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of Echeveria 'Galaxia'. These characteristics in combination distinguish 'Galaxia' as a new and distinct *Echeveria* cultivar:

1. *Echeveria* 'Galaxia' produces large, bright orange flowers, in combination with a concentric, blue-violet rosette.

2. *Echeveria* 'Galaxia' exhibits a rosette morphology comprised of leaves that are more truncate, enabling less breakage of the leaves during the shipping process.
3. *Echeveria* 'Galaxia' is freely offsetting, forming low growing clusters quickly.
4. *Echeveria* 'Galaxia' exhibits robust growth, and prolific offsetting, resulting in rapid propagation of the plant in the commercial nursery.

PARENTAL COMPARISON

Plants of the new cultivar 'Galaxia' can be compared to plants of the seed parent *Echeveria* 'ENC07', and are similar in most horticultural characteristics. However, plants of the new cultivar 'Galaxia' display larger orange flowers, as compared to the flowers of the seed parent 'ENC07' The new cultivar 'Galaxia' is early and freely offsetting, whereas the seed parent *Echeveria* 'ENC07' does not form offsets until it reaches a much larger size, and does not produce as many as the new cultivar 'Galaxia'. The new cultivar 'Galaxia' forms rosettes of cobalt blue-violet, as compared to the pallid rosettes of the seed parent Echeveria 'ENC07'.

Plants of the new cultivar 'Galaxia' can be compared to plants of the pollen parent *Echeveria* 'AG2B', and are similar in most horticultural characteristics. However, plants of the new cultivar 'Galaxia' exhibit a more concentric rosette comprised of truncate leaves, resulting in less breakage during shipping, as compared to the pollen parent *Echeveria* 'AG2B', which has longer, more slender leaves that often break at the tips. The new cultivar 'Galaxia' forms concentric cobalt blue-violet rosettes, as compared with the lax, non-concentric rosettes of the pollen parent 'AG2B'.

The new cultivar 'Galaxia' produces offsets freely and at a relatively early age, in contrast to the occasional offset produced at a later age by the pollen parent 'AG2B'.

COMMERCIAL COMPARISON

The new cultivar 'Galaxia' can be compared to the unpatented commercial variety *Echeveria* 'Afterglow '. Plants of *Echeveria* 'Afterglow' are similar to plants of the new cultivar 'Galaxia' in most horticultural characteristics. However, the new cultivar 'Galaxia' displays a more concentric rosette than does *Echeveria* 'Afterglow', resulting in a more aesthetic rosette form. In addition, 'Galaxia' produces truncate leaves, as compared to the longer, more slender leaves produced by 'Afterglow', greatly reducing leaf breakage during shipping in the commercial nursery. The new cultivar 'Galaxia' offsets at an earlier age than does *Echeveria* 'Afterglow', enhancing propagation intervals.

The new cultivar 'Galaxia' can be compared to the unpatented commercial variety *Echeveria* 'Tahiti'. Plants of *Echeveria* 'Tahiti' are similar to plants of the new cultivar 'Galaxia' in most horticultural characteristics. However, the new cultivar 'Galaxia' displays inflorescences with much larger flowers than those displayed by *Echeveria* 'Tahiti'. Plants of the cultivar 'Galaxia' produce offsets freely, and at an early age, enhancing the propagation rate, and producing morphologically aesthetic clusters, as compared to the scant offsets produced by Echeveria 'Tahiti'.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. All photographs provided by the breeder.

DETAILED BOTANICAL DESCRIPTION

Figure 1:
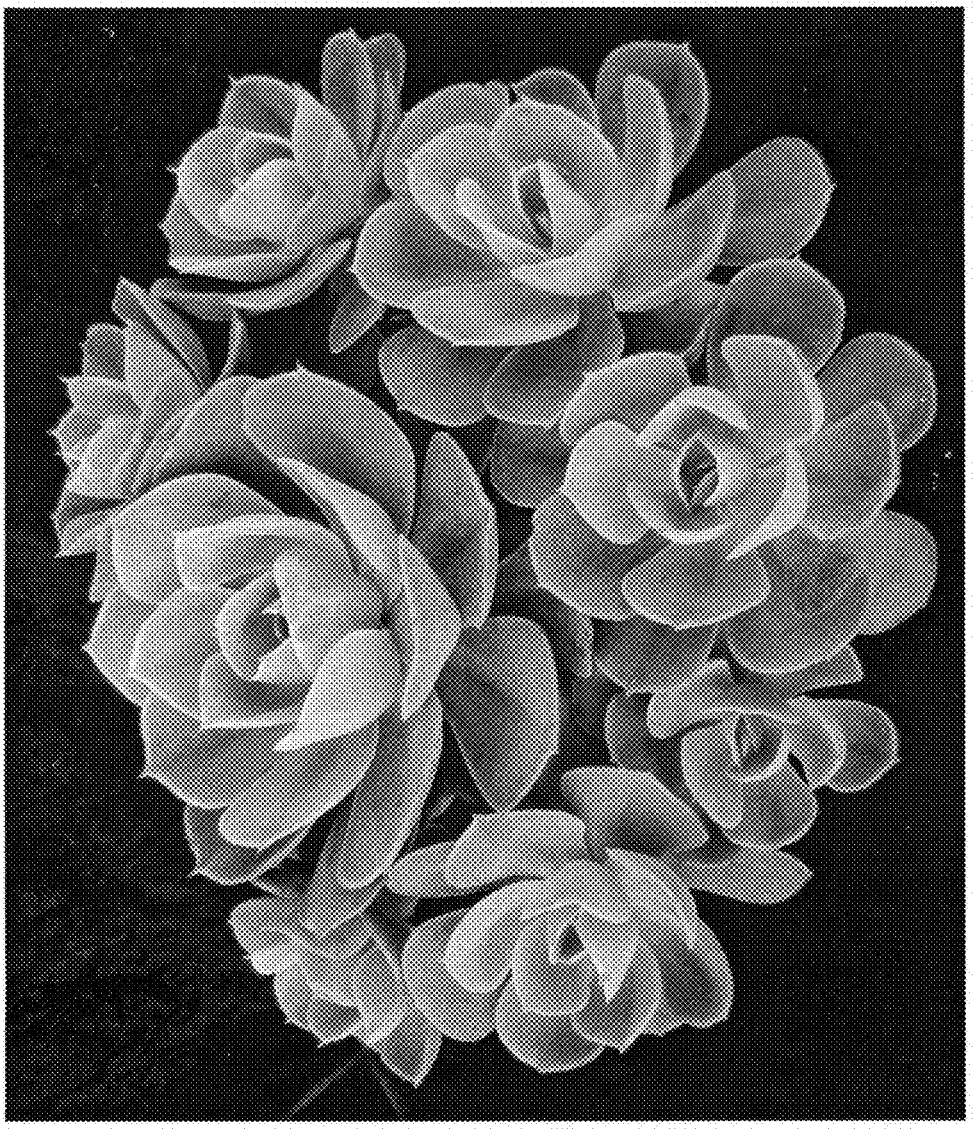
FIG. 1 illustrates in full color a rosette typical of plants of *Echeveria* 'Galaxia' grown in a greenhouse in Vista, Calif.
Figure 2:
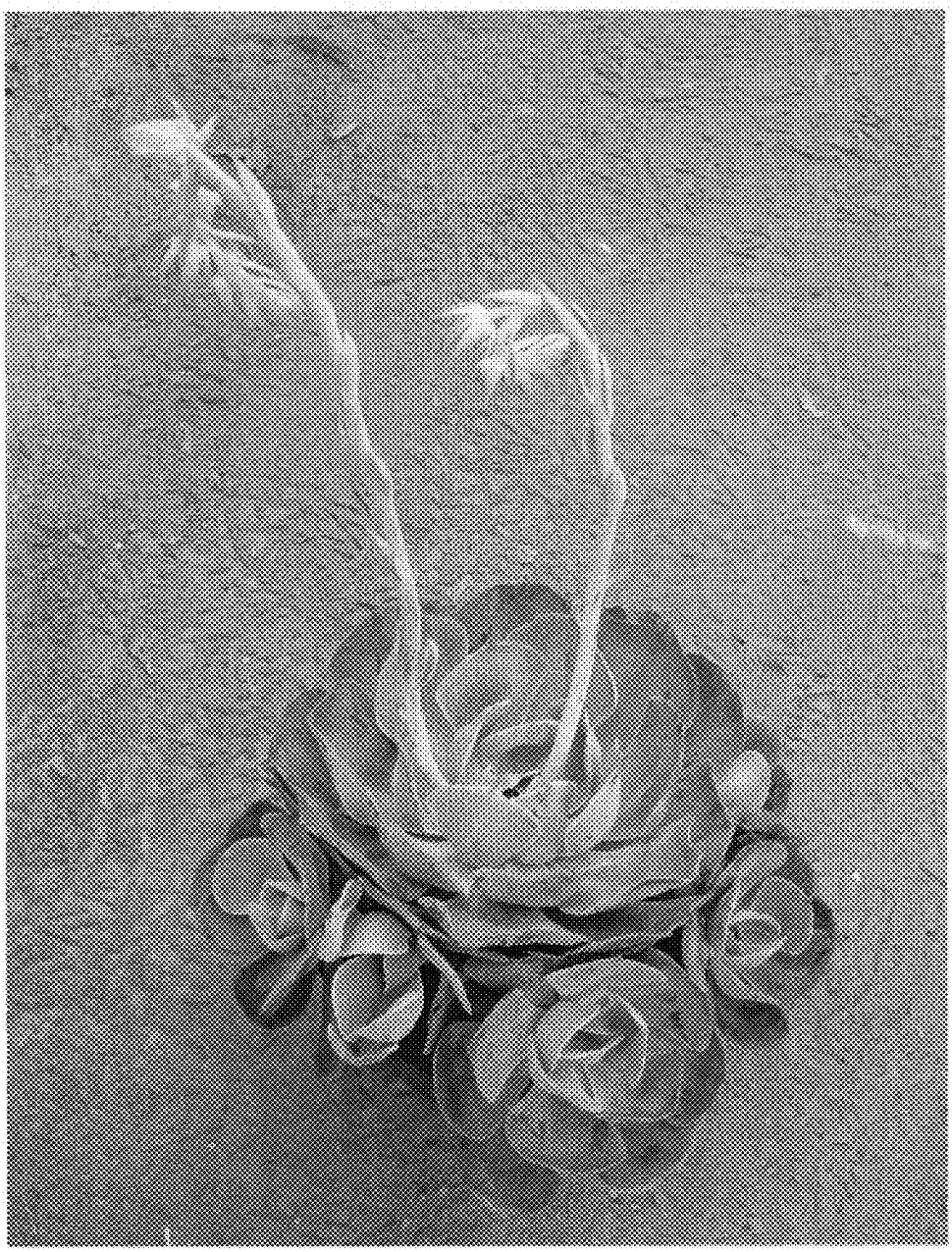
FIG. 2 illustrates in full color a plant with inflorescence typical of plants of *Echeveria* 'Galaxia' grown in a greenhouse in Vista, Calif.
Figure 3:
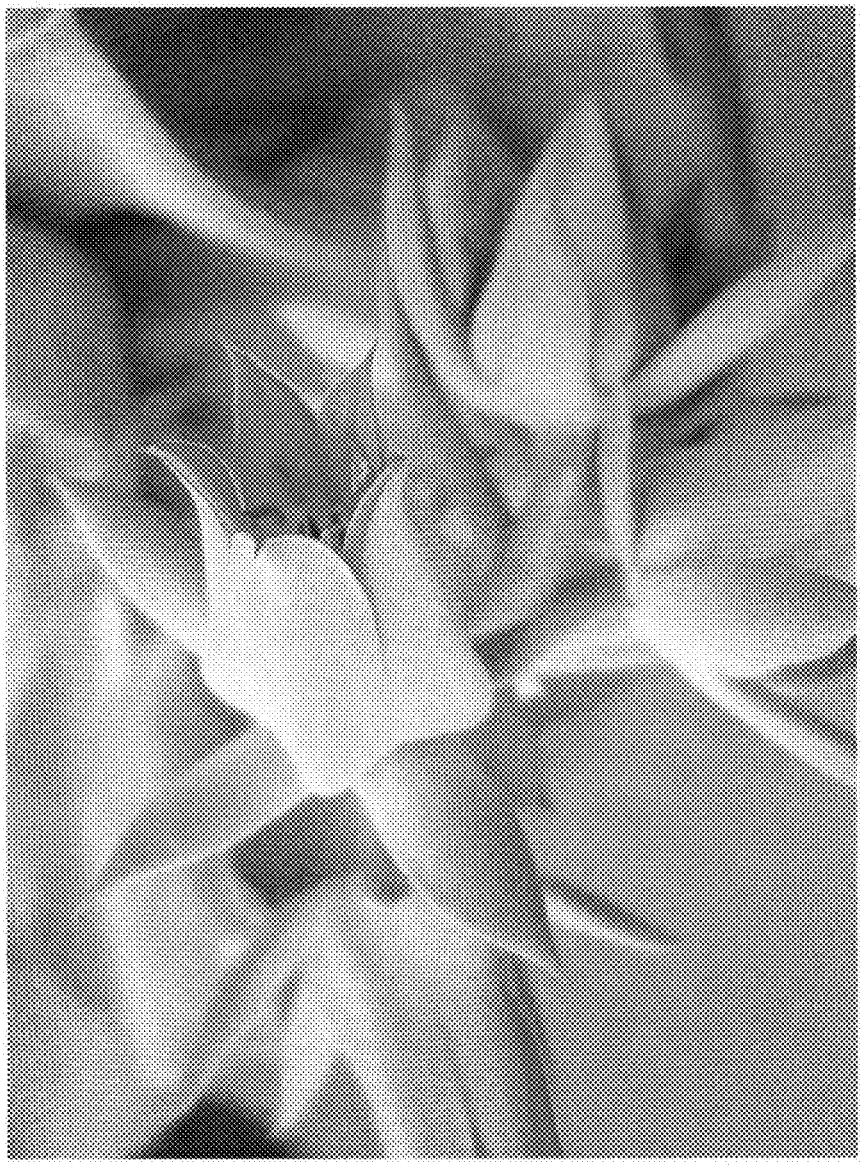
FIG. 3 illustrates in full color a close-up of the flower typical of plants of *Echeveria* 'Galaxia' grown in a greenhouse in Vista, Calif.
Figure 4:
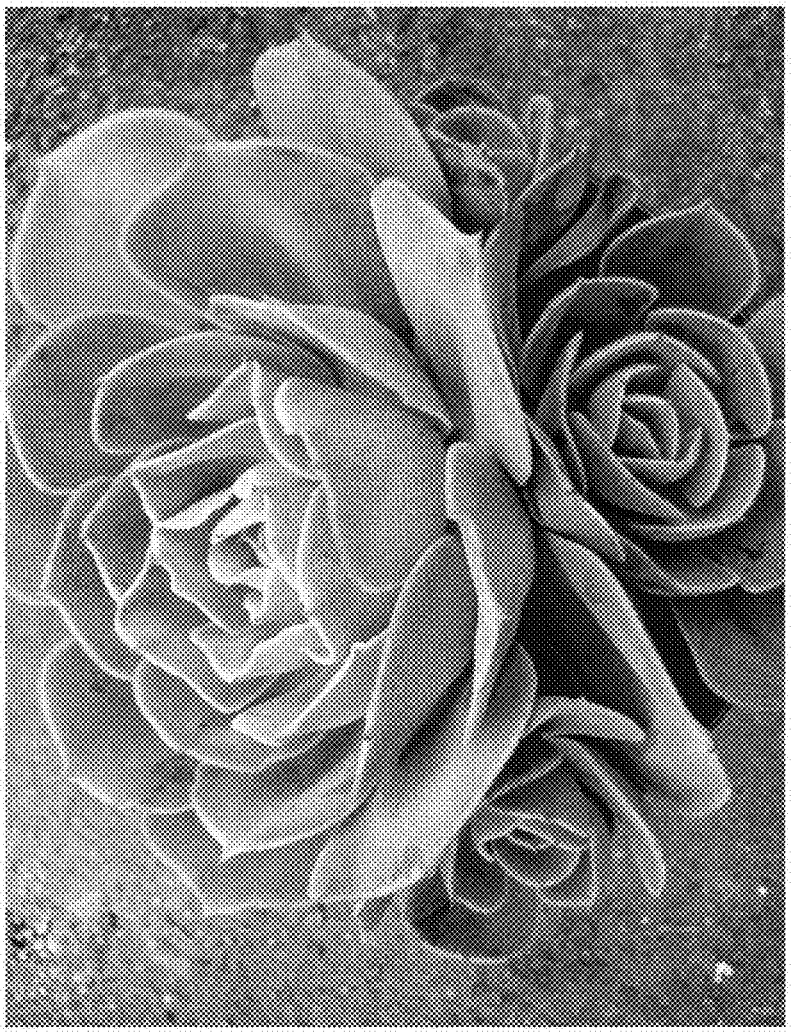
FIG. 4 illustrates in full color a rosette with offsets typical of plants of *Echeveria* 'Galaxia' grown in a greenhouse in Vista, Calif.

In the following description, color references are made to the Panton Process Color System Guide, except where general terms of ordinary dictionary significance are used. The following observations and measurements describe *Echeveria* 'Galaxia' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'Galaxia'.

Age of the plant described: Approximately 4 months from a cutting.

PROPAGATION

Time to initiate roots: About 12 days at approximately 24° C.

Root description: Fibrous.

Propagation method: Terminal vegetative cuttings.

PLANT

Growth habit: Rosulate.

Age of plant described: Approximately 4 months from a cutting.

Container size: 20.5 cm. (8").

Height: Approximately 15 cm to top of highest leaf Approximately 44 cm to top of highest inflorescence.

Plant spread: Approximately 29 cm.

Growth rate: Moderately fast.

Branching characteristics: Early and freely offsetting.

FOLIAGE

Leaf:

- *Arrangement*.—Rosulate.
- *Average length*.—Approximately 10 cm.
- *Longest length*.—Approximately 13.25 cm.
- *Average width*.—Approximately 7.5 cm.
- *Widest width*.—Approximately 9.3 cm.
- *Width at base*.—3 cm.
- *Shape of blade*.—Truncate.
- *Apex*.—Mucronate.
- *Base*.—Elliptical.
- *Margin*.—Entire.
- *Texture of top surface*.—Glabrous, glaucous.
- *Texture of bottom surface*.—Glabrous, glaucous.
- *Quantity of leaves per plant*.—Approximately 36.
- *Young foliage upper side*.—Near S 192-6 Pantone.
- *Young foliage, upper side, apical margin*.—Near S 152-4 Pantone.
- *Young foliage upper side, near base*.—Near S 257-8 Pantone.
- *Young foliage, under side*.—Near S 206-6 Pantone. Mature foliage,
- *Upper side*.—Near S 199-8 Pantone.
- *Mature foliage, upper side, towards apex of leaf*.—Near S 137-8 Pantone.
- *Mature foliage, under side*.—Near S 137-7 if glaucous layer removed, with glaucous layer is S 177-8 Pantone.
- *Mature foliage, margin, near apex*.—Near S 121-2 Pantone.
- *Mature foliage, upper side, mid-leaf margin*.—Near S 150-6 Pantone.
- *Mature foliage, upper side, near stem*.—Near S 257-8 Pantone.
- *Mature foliage, grown in full sun*.—Near S 204-7 Pantone.
- *Mature foliage, margin, grown in full sun*.—Near S 142-4 Pantone.

Venation:

- *Type*.—There is no visual appearance of venation.
- *Venation color upper side*.—If venation is present, it is Indistinguishable from overall foliage color.

*Venation color under side.*—If venation is present, it is Indistinguishable from overall foliage color.

FLOWER

Natural flowering season: May, June.

Inflorescence type and habit: Erect; composed of several simple cincinni.

Rate of flower opening: 1 every 2-3 days, dependent upon ambient conditions.

Flower longevity on plant: Flowers can last 4-5 days, dependent upon ambient conditions.

Quantity of flowers: 25.

Total inflorescence size:

*Height.*—Approximately 37 cm.

*Width.*—Approximately 19.25 cm.

Corolla:

*Arrangement.*—5-merous.

*Size.*—Length — Approximately 2.4 cm. Width — Approximately 1.8 cm at flared tip (widest point) base is 1.5 cm. horn to horn. Lobe Length — Approximately 2.6 cm. Lobe width — Approximately 0.75 cm.

*Margin.*—Entire.

*Shape.*—Almost cylindrical.

*Apex.*—Acute.

*Texture.*—Glabrous.

*Color.*—Petals: When opening: Outer surface, near apex — Near S 124-3 Pantone. Outer surface, near base — Near S 128-5 Pantone. Inner surface, near apex — Near S 73-1 Pantone. Inner surface, mid petal — Near S 73-5 Pantone.

Corolla:

*Petal color, fully opened.*—Outer surface — Near S 97-4 Pantone. Outer surface, apex — Near S 124-3 Pantone. Inner surface, mid petal — Near S 49-1 Pantone. Inner surface, apex — Near S 73-3 Pantone. Color Changes when Aging — Near S 124-3 Pantone. Near S 72-3 Pantone at apex of petal. Near S 124-4 Pantone near base of petal.

Bud: (near opening):

*Shape.*—Conical.

*Length.*—Approximately 1.5 cm.

*Diameter.*—Approximately 1.3 cm.

*Color, apex of bud.*—Near S 182.6 Pantone.

*Color, mid bud.*—Near S 114-6 to S 114-7 Pantone.

*Color, base of bud.*—Near S 286-7 Pantone.

Sepals:

*Color, sepal, outer.*—Near S 206-6 Pantone.

*Color, sepal, inner.*—Near S 206-4 Pantone.

Pedicels:

*Length.*—Approximately 1.0 cm.

*Width.*—Approximately 0.3 cm.

*Aspect.*—Ascending.

*Color.*—Near S 177-6 Pantone.

*Fragrance.*—None detected.

REPRODUCTIVE ORGANS

Stamens: (Androecium).

*Number.*—Average 10.

*Filament length.*—Approximately 0.9 cm.

*Filament color.*—Near S 18-6 Pantone.

*Anther length.*—0.275 cm.

*Anther color.*—Near S 66-2 Pantone.

*Anther shape.*—Oblong.

*Pollen color.*—Between S 18.7 Pantone & S 18.6 Pantone.

Pistil: (Gynoecium).

*Number.*—Average 5.

*Length.*—Approximately 1.0 cm.

*Style color.*—Near S 137-3 Pantone.

*Stigma.*—Shape — Round. Color — Near S 137-1 Pantone. Ovary Color — Near S 2-8 Pantone.

OTHER CHARACTERISTICS

Fruits and seeds: Typical to Genus. Minute, approximately 1 mm dry seeds. Colored between black and brown, too small to accurately measure with color chart.

Temperature tolerance: Tolerates temperatures from approximately −2 C to at least 35 C.

Disease/pest resistance: Neither resistance or susceptibility to normal diseases and pests of *Echeveria* has been observed.

Drought tolerance : Tolerates at least 3 weeks of high temperatures without supplemental water, showing no serious damage to plant.

What is claimed is:

1. A new and distinct cultivar of *Echeveria* plant named 'Galaxia' as herein illustrated and described.

* * * * *